(12) United States Patent
Chevallier

(10) Patent No.: US 7,678,086 B2
(45) Date of Patent: Mar. 16, 2010

(54) SAFETY INJECTION DEVICE FOR SYRINGE

(75) Inventor: Stëphane Chevallier, Saint-Pathus (FR)

(73) Assignee: Tech Group Europe Limited, Dublin (IE)

( * ) Notice: Subject to any disclaimer, the term of this patent is extended or adjusted under 35 U.S.C. 154(b) by 795 days.

(21) Appl. No.: 10/577,380

(22) PCT Filed: Oct. 13, 2004

(86) PCT No.: PCT/FR2004/002597

§ 371 (c)(1),
(2), (4) Date: Aug. 23, 2006

(87) PCT Pub. No.: WO2005/046772

PCT Pub. Date: May 26, 2005

(65) Prior Publication Data

US 2007/0088287 A1    Apr. 19, 2007

(30) Foreign Application Priority Data

Oct. 29, 2003    (FR)    ................................ 03 12642

(51) Int. Cl.
*A61M 5/32*    (2006.01)
(52) U.S. Cl. .................................................. 604/198
(58) Field of Classification Search ......... 604/110–111, 604/192–198
See application file for complete search history.

(56) References Cited

U.S. PATENT DOCUMENTS

| 5,201,708 | A  | * | 4/1993  | Martin .................. 604/110 |
| 6,319,233 | B1 | * | 11/2001 | Jansen et al. ........... 604/192 |
| 6,613,022 | B1 |   | 9/2003  | Doyle |
| 2002/0156426 | A1 |   | 10/2002 | Gagnieux et al. |

FOREIGN PATENT DOCUMENTS

| FR | 2 830 765 | 4/2003 |
| FR | 2 835 753 | 8/2003 |
| WO | WO 01/41841 A2 | 6/2001 |

* cited by examiner

*Primary Examiner*—Nicholas D Lucchesi
*Assistant Examiner*—Christopher D Koharski
(74) *Attorney, Agent, or Firm*—Panitch Schwarze Belisario & Nadel LLP

(57) ABSTRACT

The device comprises a support sheath (14), a syringe body (10) secured to said sheath, and a protection sheath (16) movable between a retracted position and an extended protection position. The device includes retaining means (17) for retaining the protection sheath that are adapted to be urged so as to allow the sheath to be extended. The syringe body (10) is secured to the support sheath (14) via a ring (20) including a coupling wall (22) that is substantially transverse. This wall presents at least one slot (23) enabling the retaining means to be acted upon from the side of the coupling wall (22) that is opposite from the distal end of the support sheath.

15 Claims, 3 Drawing Sheets

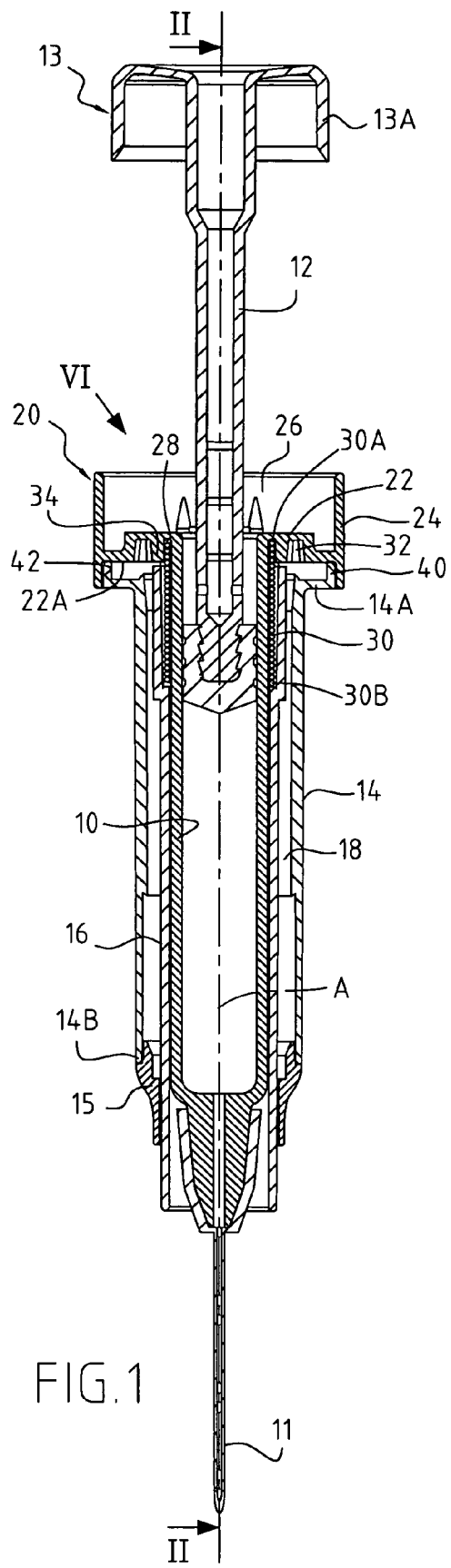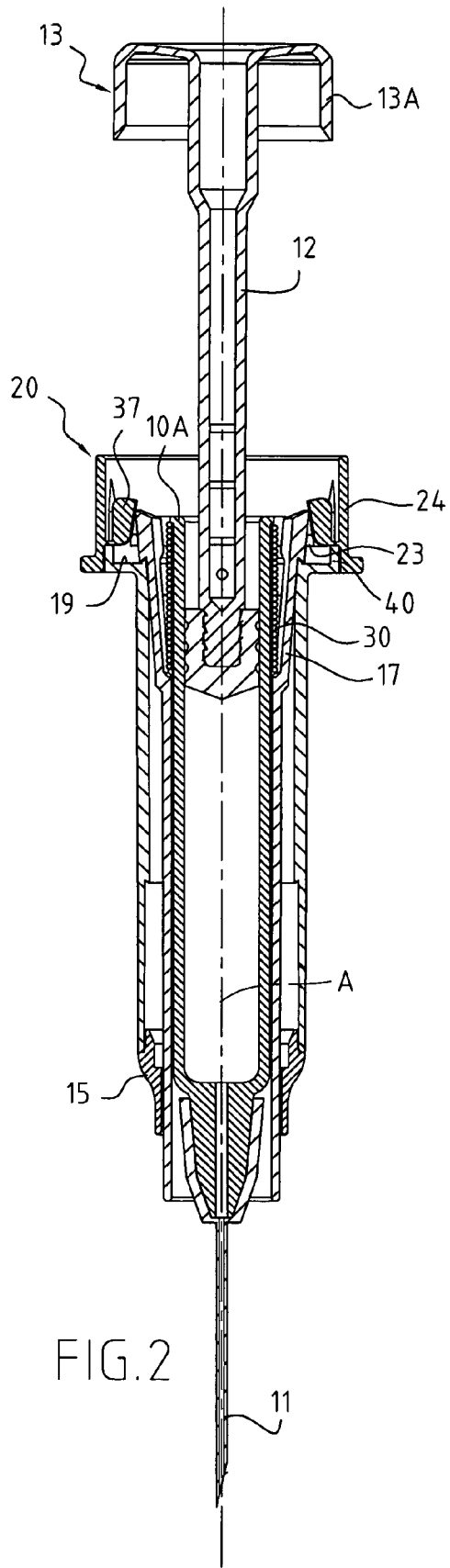

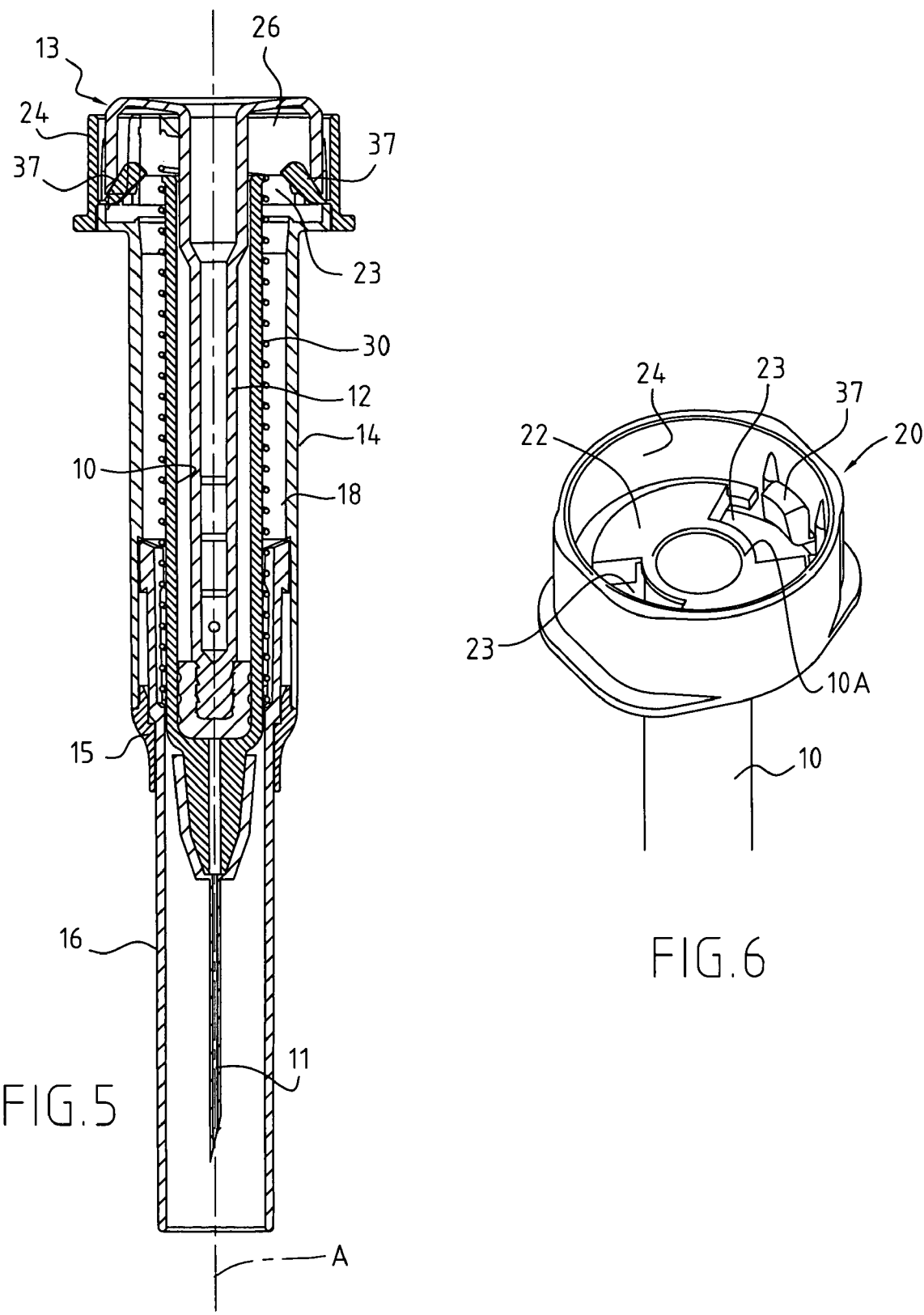

SAFETY INJECTION DEVICE FOR SYRINGE

This is a 371 national phase application of PCT/FR2004/002597 filed 13 Oct. 2004, claiming priority to French Patent Application No. FR 0312642 filed 29 Oct. 2003, the contents of which are incorporated herein by reference.

The present invention relates to a safe injection device comprising a support sheath having a proximal end and a distal end, a syringe body secured to said support sheath, and a protection sheath suitable for sliding axially between a retracted position in which it is retracted into an annular space formed between the syringe body and the support sheath, and an extended protection position in which it projects beyond the distal end of the support sheath, the device further comprising retaining means suitable for adopting an active retaining configuration for retaining the protection sheath in the retracted position and, starting from said active configuration, suitable for being urged so as to allow the protection sheath to be extended under drive from thrust means.

Devices of this type are disclosed in documents WO 01/41841 and WO 03/068298.

In those prior art devices, the support sheath and the protection sheath are assembled and premounted, and then the syringe body, generally made of glass, is inserted into the premounted assembly in which it is held by snap-fastening. That mounting operation is thus performed after the support sheath and the protection sheath have been assembled together. It therefore requires special equipment that is distinct from the equipment used for fabricating and assembling the support sheath and the protection sheath.

Such an operation can be desirable when the syringe body, prefilled with liquid for injection and sterilized, is inserted into the premounted assembly comprising the support sheath and the protection sheath. Nevertheless, in certain applications, the syringe body can be put into place while it is empty. With the above-mentioned prior art devices, even when the body is empty, it is necessary to fabricate and assemble the support sheath and the protection sheath, and to put the syringe body into place therein during a distinct step, in general on a site different from the fabrication site, and to fill the body prior to making an injection.

The present invention seeks to simplify that process by proposing a device that makes it possible to avoid the step of putting the syringe body into place after fabricating and assembling the support and protection sheaths.

This object is achieved by the fact that the syringe body is secured to the support sheath via a ring having a coupling wall that extends substantially transversely between the syringe body and the support sheath, said wall presenting at least one slot enabling the retaining means to be acted upon from the side of the coupling wall that is opposite from the distal end of the support sheath.

With this device, the assembly constituted by the two sheaths and the syringe body is assembled together because of the presence of the above-specified ring. Thus, the syringe body is put into place at the same time as the support and protection sheaths and forms a part of the device as soon as it has been fabricated. Because of the particular confirmation of the coupling ring, which presents at least one slot, the means for retaining the protection sheath that enable it to be passed into the active configuration can easily be acted upon, as in patent applications WO 01/41841 and WO 03/068298.

In particular, this action on the retaining means can be performed by the head of the injection piston. The piston can be put into place inside the syringe body at the time the various component elements of the device are assembled together by being pushed towards the distal end. The syringe body can be filled with the liquid for injection at a later time, by pulling the piston towards the proximal end of the device. The syringe needle can be put into place at the time the device is used. The needle can be used for a single use or optionally it can be sterilized between two uses. It may be used, for example, to take blood samples or to perform injections of the kind performed by a syringe that is not prefilled, the syringe being filled immediately prior to making the injection.

In a preferred embodiment, the ring is formed integrally with the support sheath and/or with the syringe body.

Advantageously, when the ring constitutes a part that is distinct from at least one of the elements constituted by the syringe body and by the support sheath, and said ring and said element present respective fastener skirts, said skirts coming into contact with each other via axial surfaces whereby the ring and said element are fastened together.

Advantageously, the retaining means comprise at least one retaining tab which passes through the slot in the coupling wall and which can be acted upon from the side of said wall that is remote from the distal end of the support sheath; for this purpose, the tab advantageously extends through the coupling wall.

The method of fastening together the ring and the element that is distinct therefrom, i.e. the syringe body or the support sheath, is advantageously selected from heat-sealing, interfitting, a force-fit, and adhesive.

The invention can be well understood and its advantages appear better on reading the following detailed description of an embodiment given by way of non-limiting example. The description refers to the accompanying drawings, in which:

FIG. 1 is an axial section view of the device of the invention prior to an injection, the protection sheath being in its retracted position;

FIG. 2 is a section view on line II-II of FIG. 1;

FIGS. 4 and 5 are axial section views respectively in the same planes as FIG. 1 and as FIG. 2, showing the protection sheath in its extended protection position; and FIG. 6 is a perspective view seen looking along arrow VI of FIG. 1 showing the coupling ring and the end portion of the syringe body which is formed integrally with said ring.

The device shown in the figures comprises a syringe having a syringe body 10, a needle 11, and a piston 12 that can slide in the body to make an injection. In FIGS. 1 and 2, the piston is in a rear position, i.e. it has been pulled back from the distal end towards the proximal end, and the device is shown prior to making an injection.

Figure 3:
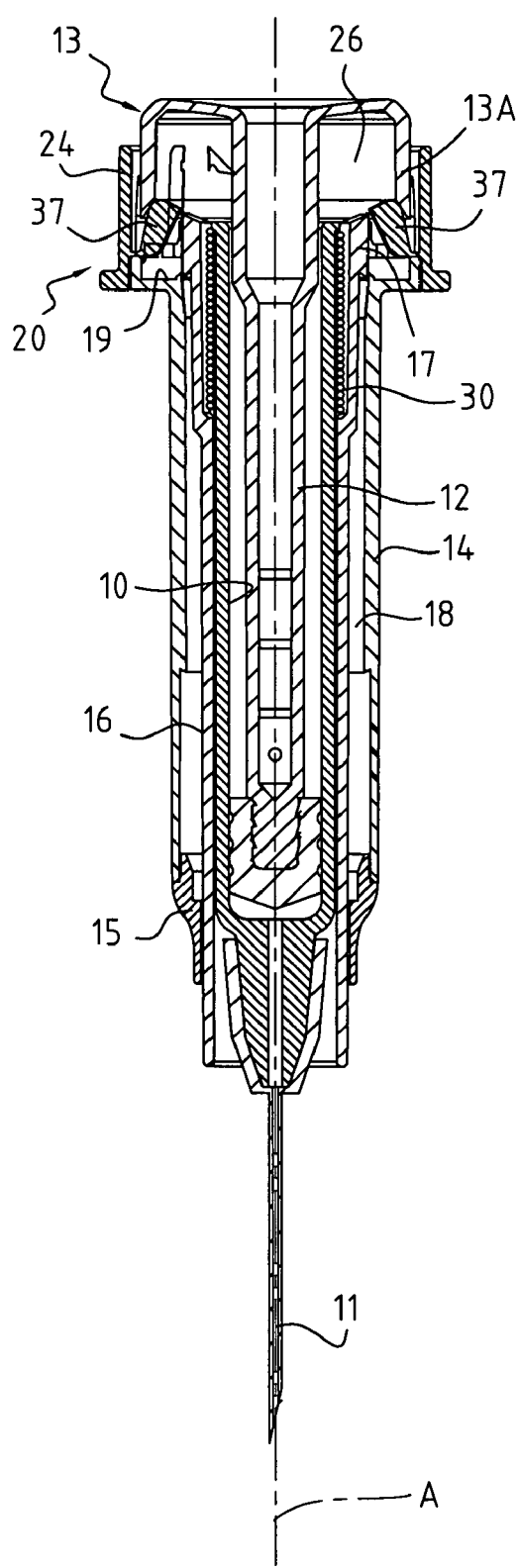
FIG. 3 is a view in the same section plane of FIG. 2, showing the action applied to the means for retaining the protection sheath at the end of injection.

The device also comprises a support sheath 14 and a protection sheath 16 which, in FIGS. 1 to 3, is shown in its retracted position, in which it extends essentially in an annular space 18 formed between the syringe body 10 and the support sheath 14.

The syringe body 10 is secured to the support sheath 14 via a ring 20 that includes a coupling wall 22 that extends substantially transversely between the syringe body and the support sheath. Specifically, this ring is connected to the support sheath via the proximal end 14A thereof. The ring 20 is formed integrally with the syringe body 10.

Figure 4:
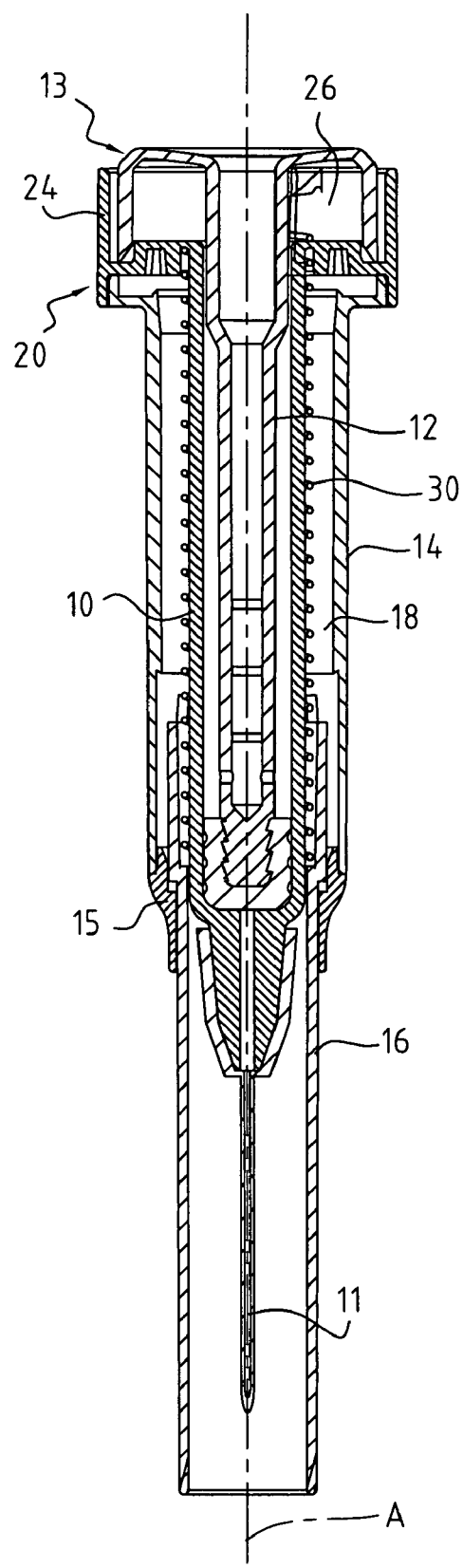

The ring presents an outer axial wall 24 that extends beyond the coupling wall 22 in a rearward direction and defines a housing 26 in which the actuator head 13 of the piston becomes substantially received at the end of an injection stroke, as can be seen in FIGS. 4 and 5.

In its inside face 22A facing towards the distal end 14B of the support sheath 14, the coupling wall 22 of the ring 20 presents a setback 28 in which the proximal end 30A of a thrust spring 30 is placed, the distal end 30B of the spring bearing against the protection sheath 16.

To this end, the wall of the protection sheath presents a step providing an inside shoulder.

Specifically, the setback 28 is formed by an annular groove serving to hold the end 30A of the spring 30 both axially and radially.

The coupling wall 22 also presents another annular groove 32 serving to increase the apparent thickness of this wall and maintain its strength while, as much as possible, conserving a thickness of material that is substantially constant so as to allow cooling to take place uniformly during unmolding. The coupling wall 22 presents at least one reinforcing rib, which is formed specifically by the rib 24 that extends between the annular grooves 28 and 32.

In its retracted position, the protection sheath 16 is held relative to the support sheath 14 by retaining means comprising at least one retaining tab that is secured to the protection sheath, and the device includes at least one retaining surface for said tab which is stationary relative to the syringe body 10, the retaining tab being retained on the retaining surface when said tab is in its active retaining configuration and being capable of being moved so as to escape from said surface. Specifically, two diametrically-opposite retaining tabs 17 are present, and the two retaining surfaces are formed by two diametrically-opposite zones of a shoulder 19.

The retaining tabs 17 are situated at the proximal end of the protection sheath 16. These tabs are resilient and they tend naturally to spread away from the axis A of the device so as to catch on the inside shoulder 19 facing towards the rear of the support sheath. In this position, they naturally prevent the protection sheath 16 form moving forwards, i.e. towards the distal end of the support sheath.

In order to enable the tabs 17 to be acted upon from the side of the coupling wall 22 that is remote from the distal end of the support sheath, said wall 22 presents two diametrically-opposite slots 23, as can be seen more clearly in FIG. 6. It is through these slots of closed outline that the proximal ends of the tabs 17 can be acted upon so as to push the tabs towards the axis A, thereby releasing the shoulder 19 so as to allow the protection sheath to be extended under the effect of the thrust exerted by the spring 30, so that the sheath reaches its extended protection position as shown in FIGS. 4 and 5.

The injection piston 12 is secured to a trigger member that is adapted, at the end of the piston injection stroke, to release the action on the retaining means outside their active configuration. Specifically, this trigger member is formed by a skirt 13A of the head 13 of the piston.

The ring 20 presents at least one transmission tab that is adapted to be moved by said trigger member in order to drive the retaining means away from their active configuration.

Specifically, the ring 20 has two diametrically-opposite transmission tabs 37 that are disposed in the vicinity of the above-mentioned slots 23 in the wall 22. As can be seen in FIGS. 2 and 6, the transmission tabs 37 naturally occupy a position in which they extend substantially axially towards the rear of the ring 20.

Thus, as shown in FIG. 3, the skirt 13A of the head 13 of the piston comes into contact with the transmission tabs 37 at the end of injection and tends to push them towards the axis A of the device. These tabs 37 then push the retaining tabs 17 so as to release them from the shoulder 19.

When they are pushed towards the axis A, the tabs 37 extend substantially through the slots 23.

In the embodiment shown in the drawings, the ring 20 is formed integrally with the syringe body 10 and the coupling wall 22 is coupled to the free proximal end 10A of the body 10. In contrast, the ring 20 constitutes a part that is separate from the support sheath 14. At its proximal end 14A, the sheath 14 presents a fastener skirt 40 that extends rearwards in a substantially axial direction. The ring 20 also presents a fastener skirt 42 that extends forwards from the coupling wall 22. These skirts come into contact with each other along axial surfaces whereby the ring and the support sheath are fastened together. Specifically, the skirt 42 is placed outside the skirt 40. The contacting axial surfaces are thus the inside axial surface of the skirt 42 and the outside axial surface of the skirt 40. An inverse disposition could nevertheless be adopted.

Because of this disposition, the contact surface between firstly the first part constituted by the syringe body 10 together with the ring 20 and, secondly the second part constituted by the support sheath 14 is large enough to enable these two parts to be fastened together safely. In particular, it is possible to use fastening by means of a force-fit. This fastening may optionally be made safe by heat-sealing or by adhesive, should that be necessary. Fastening by mutual engagement, possibly including snap-fastening, could also be used, in which case the contacting axial surfaces may present respectively a projecting element such as a rib and a reentrant element such as a groove, the elements cooperating together by snap-fastening.

With the invention, the syringe body 10 and the ring 20 can be formed as a single piece by molding or injection molding, and the protection sheath may also be made by molding or by injection molding prior to these two parts being coupled together. Specifically, it can be seen that that the distal end 14B of the support sheath 14 carries an endpiece 15 which closes the annular space 18 at the distal end of the device. This endpiece may be fitted to the end of the support sheath 14 and may be fastened thereto, e.g. as a force-fit, by heat-sealing, by adhesive, or by mutual engagement.

In a variant, provision could be made for the ring 20 to be made integrally with the support sheath 14 and for the endpiece formed in this way to be secured to the syringe body 10, constituting a separate part, and using the above-mentioned fastening techniques. It is also possible to make provision for the syringe body 10, the ring 20, and the support sheath 14 (not including its endpiece 15) to be made as a single piece, e.g. by injection molding. Under such circumstances, at least one moving insert in the form of a tube can be placed in the annular space 18 in order to preserve its shape during molding.

The invention claimed is:

1. A safe injection device comprising a support sheath having a proximal end and a distal end, a syringe body secured to said support sheath, and a protection sheath suitable for sliding axially between a retracted position in which said protection sheath is retracted into an annular space formed between the syringe body and the support sheath, and an extended protection position in which said protection sheath projects beyond the distal end of the support sheath, the device further comprising at least one retaining member suitable for adopting an active retaining configuration for retaining the protection sheath in the retracted position and, starting from said active configuration, suitable for being urged so as to allow the protection sheath to be extended, the syringe body being secured to the support sheath via a ring having a coupling wall that extends substantially transversely between the syringe body and the support sheath, said wall presenting at least one slot enabling the retaining means to be acted upon from a side of the coupling wall that is opposite from the distal end of the support sheath, and the ring being formed integrally with at least one of the support sheath and the syringe body, wherein the ring constitutes a part that is distinct from at least one of the elements constituted by the syringe body and by the support sheath, and wherein the ring and said element present respective fastener skirts, said skirts coming into contact with each other via axial surfaces whereby the ring and said element are fastened together.

2. A device according to claim 1, wherein the ring is formed integrally with the syringe body.

3. A device according to claim 1, wherein the ring constitutes a part that is distinct from at least one of the elements constituted by the syringe body and by the support sheath and is fastened to said element by a fastening technique selected from heat-sealing, mutual engagement, a force-fit, and adhesive.

4. A safe injection device comprising a support sheath having a proximal end and a distal end, a syringe body secured to said support sheath, and a protection sheath suitable for sliding axially between a retracted position in which said protection sheath is retracted into an annular space formed between the syringe body and the support sheath, and an extended protection position in which said protection sheath projects beyond the distal end of the support sheath, the device further comprising at least one retaining member suitable for adopting an active retaining configuration for retaining the protection sheath in the retracted position and, staffing from said active configuration, suitable for being urged so as to allow the protection sheath to be extended, the syringe body being secured to the support sheath via a ring having a coupling wall that extends substantially transversely between the syringe body and the support sheath, said wall presenting at least one slot enabling the retaining means to be acted upon from a side of the coupling wall that is opposite from the distal end of the support sheath, and the ring being formed integrally with at least one of the support sheath and the syringe body, wherein the at least one retaining member comprises at least one retaining tab that passes through the slot and that extends through the coupling wall.

5. A device according to claim 4, further comprising an injection piston, which is secured to a trigger member adapted, at the end of the piston injection stroke, to trigger urging the retaining means away from their active configuration.

6. A device according to claim 5, wherein the ring presents at least one transmission tab adapted to be displaced by the trigger member to urge the at least one retaining member away from the active configuration thereof.

7. A device according to claim 4, wherein the ring is formed integrally with the syringe body.

8. A device according to claim 4, wherein, in an inside face thereof facing towards the distal end of the support sheath, the coupling wall presents a setback in which the proximal end of a thrust spring is disposed, the distal end of the thrust spring bearing against the protection sheath.

9. A device according to claim 4, wherein the coupling wall presents at least one reinforcing rib.

10. A safe injection device comprising a support sheath having a proximal end and a distal end, a syringe body secured to said support sheath, and a protection sheath suitable for sliding axially between a retracted position in which said protection sheath is retracted into an annular space formed between the syringe body and the support sheath, and an extended protection position in which said protection sheath projects beyond the distal end of the support sheath, the device further comprising at least one retaining member suitable for adopting an active retaining configuration for retaining the protection sheath in the retracted position and, starting from said active configuration, suitable for being urged so as to allow the protection sheath to be extended, the syringe body being secured to the support sheath via a ring having a coupling wall that extends substantially transversely between the syringe body and the support sheath, said wall presenting at least one slot enabling the retaining means to be acted upon from a side of the coupling wall that is opposite from the distal end of the support sheath, and the ring being formed integrally with at least one of the support sheath and the syringe body, wherein the at least one retaining member comprises at least one retaining tab that is secured to the protection sheath and the device including at least one retaining surface for said tab which is stationary relative to the syringe body, the retaining tab being retained on the retaining surface when said tab is in the active retaining configuration thereof and being capable of being displaced to escape from said surface.

11. A device according to claim 10, wherein the ring is formed integrally with the syringe body.

12. A device according to claim 10, wherein, in an inside face thereof facing towards the distal end of the support sheath, the coupling wall presents a setback in which the proximal end of a thrust spring is disposed, the distal end of the thrust spring bearing against the protection sheath.

13. A device according to claim 10, wherein the coupling wall presents at least one reinforcing rib.

14. A device according to claim 10, further comprising an injection piston, which is secured to a trigger member adapted, at the end of the piston injection stroke, to trigger urging the retaining means away from their active configuration.

15. A device according to claim 14, wherein the ring presents at least one transmission tab adapted to be displaced by the trigger member to urge the at least one retaining member away from the active configuration thereof.

\* \* \* \* \*